United States Patent [19]
Dixon et al.

[11] Patent Number: 5,750,399
[45] Date of Patent: May 12, 1998

[54] ISOFLAVONE REDUCTASE PROMOTER

[75] Inventors: Richard A. Dixon; Nancy L. Paiva, both of Ardmore, Okla.; Abraham Oommen, Lincoln, Nebr.

[73] Assignee: The Samuel Roberts Noble Foundation, Inc., Ardmore, Okla.

[21] Appl. No.: 339,129

[22] Filed: Nov. 14, 1994

[51] Int. Cl.$^6$ ............................. C12N 5/04; C12N 15/29; C12N 15/82; A01H 5/00
[52] U.S. Cl. .................. 435/419; 435/172.3; 435/189; 435/320.1; 536/23.2; 536/23.6; 536/24.1; 800/205
[58] Field of Search .................. 536/23.2, 23.6, 536/24.1; 435/172.3, 189, 240.4, 320.1, 419; 800/205

[56] References Cited

FOREIGN PATENT DOCUMENTS 0255378 2/1988 European Pat. Off. ......... C12N 15/00

OTHER PUBLICATIONS

Oommen, et al., "Analysis of genomic clone for isoflavone reductase—a defense response gene from alfalfa," *J Cell Biochem*, Suppl 0, 46 Part F, p. 220, abstract Y222 (1992).
Paiva, et al., "Regulation of isoflavonoid metabolism is alfalfa," *Plant Cell Tissue and Organ Culture* 38:213–220 (1994).
Benfey, PN and Chua, NH, "Regulated genes in transgenic plants," *Science* 244:174–181 (1989).
Binns, et al., "Cell division promoting activity of naturally occurring dehydrodiconiferyl glucosides: do cell wall components control cell division?" *Proc Natl Acad Sci USA* 84:980–984 (1987).
Breathnach, U and Chambon, P, "Organization and expression of eukaryotic split genes coding for proteins," *Annu Rev Biochem* 50:349–383 (1981).
Burnett, et al., "Expression of a 3–hydroxy-3-methylglutaryl coenzyme A reductase gene from *Camptotheca acuminata* is differentially regulated by wounding and methyl jasmonate," *Plant Physiol* 103:41–48 (1993).
da Costa e Silva, et al., "BPF–1, a pathogen–induced DNA–binding protein involved in the plant defense response," *Plant J* 4:125–135 (1993).
Dickey, et al., "Light regulatory sequences are located within the 5' portion of the Fed-1 message sequence," *EMBO J* 11:2311–2317 (1992).
Dietrich, et al., "Downstream DNA sequences are required to activate a gene expressed in the root cortex of embryos and seedlings," *Plant Cell* 4:1371–1382 (1992).
Dixon, et al., "Phytoalexins: enzymology and molecular biology," *Adv Enzymol Related Areas Mol Biol* 55:1–135 (1983).
Dixon, RA and Harrison, MJ, "Activation, structure and organization of genes involved in microbial defense in plants," *Adv Genetics* 28:165–234 (1990).

Douglas, et al., "Exonic sequences are required for elicitor and light activation of a plant defense gene, but promoter sequences are sufficient for tissue specific expression," *EMBO J* 10:1767–1775 (1991).
Drews, et al., "Regional and cell–specific gene expression patterns during petal developments," *Plant Cell* 4:1383–1404 (1992).
Fritze, et al., "Developmental and UV light regulation of the snapdragon chalcone synthase promoter," *Plant Cell* 3:893–905 (1991).
Harrison, et al., "Characterization of a nuclear protein that binds to three elements within the silencer region of a bean chalcone synthase gene promoter," *Proc Natl Acad Sci USA* 88:2515–2519 (1991).
Hirsch, et al., "Bacterial–induced changes in plant form and function," *Int J Plant Sci* 153:S171–S181 (1992).
Jacobs, M. and Rubery, PH, "Naturally occurring auxin transport regulators," *Science* 241:346–349 (1988).
Jefferson, et al., "GUS fusions: β–glucuronidase as a sensitive and versatile gene fusion marker in higher plants," *EMBO J* 6:3901–3907 (1987).
Kessman, et al., "Stress responses in alfalfa (*Medicago sativa* L.) V. Constitutive and elicitor–induced accumulation of isoflavonoid conjugates in cell suspension cultures," *Plant Physiology* 94:227–232 (1990).
Lamb, et al., "Signals and transduction mechanisms for activation of plant defenses against microbial attack," *Cell* 56:215–224 (1989).
Liang, et al., "Developmental and environmental regulation of a phenylalanine ammonia–lyase–β–glucuronidase gene fusion in transgenic tobacco plants," *Proc Natl Acad Sci USA* 86:9284–9288 (1989).
Lindsay, et al., eds., "Microbial recognition and activation of plant defense systems," *Trends Microbiol* 1:181–187 (1993).
Loake, et al., "Combination of H–box [CCTACC(N)$_7$CT] and G–box [CACGTG] cis elements is necessary for feed–forward stimulation of a chalcone synthase promoter by the phenylpropanoid pathway intermediate p–coumaric acid," *Proc Natl Acad Sci USA* 89:9230–9234 (1992).
Lois, et al., "A phenylalanine ammonia–lyase gene from parsley; structure, regulation and identification of elicitor and light responsive cis–acting elements," *EMBO J.* 8:1641–1648 (1989).
Mason, et al., "Identification of a methyl jasmonate–responsive domain in the soybean vspB promoter," *Plant Cell* 5:241–251 (1993).
McElroy, et al., "Isolation of an efficient actin promoter for use in rice transformation," *Plant Cell* 2:163–171 (1990).

(List continued on next page.)

*Primary Examiner*—David T. Fox
*Attorney, Agent, or Firm*—Sidley & Austin

[57] ABSTRACT

The invention relates to a promoter and associated control elements derived from the isoflavone reductase gene. The upstream activating region and portions thereof have been characterized as to their ability to control the transcription of operably linked foreign structural genes in legumes as well as in plants which lack the isoflavonoid pathway.

39 Claims, 7 Drawing Sheets

OTHER PUBLICATIONS

Ohl, et al., "Functional properties of a phenylalanine ammonia-lyase promoter from Arabidopsis," *Plant Cell* 2:837–848 (1990).

Oppermann, et al., "Root-knot nematode-directed expression of plant root-specific gene," *Science* 263:221–223 (1994).

Paiva, et al., "Stress responses in alfalfa (*Medicago sativa* L.) 11. Molecular cloning and expression of alfalfa isoflavone reductase, a key enzyme of isoflavonoid phytoalexin biosynthesis," *Plant Mol Biol* 17:653–667 (1991).

Paiva, et al., "Molecular cloning of isoflavone reductase from pea (*Pisum sativum* L.): evidence for a 3R-isoflavanone intermediate in (+)-pisatin biosynthesis," *Archives Biochem Biophys* 312:501–510 (1994).

Pankhurst, CE and Biggs, DR, "Sensitivity of Rhizobium to selected isoflavonoids," *Can J Microbiol* 26:542–545 (1980).

Schmid, et al., "Developmental and environmental regulation of a bean chalcone synthase promoter in transgenic tobacco," *Plant Cell* 2:619–631 (1990).

Somssich, et al., "Differential early activation of defense-related genes in elicitor-treated parsley cells," *Plant Mol Biol* 12:227–234 (1989).

Stermer, et al., "Infection and stress activation of bean chalcone synthase promoters in transgenic tobacco," *Mol Plant-Microbe Interact* 3:381–388 (1990).

Sullivan, et al., "Post-transcriptional regulation of nuclear-encoded genes in higher plants: the roles of mRNA stability and translation," *Plant Mol Biol* 23:1091–1104 (1993).

Tiemann, et al., "Pterocarpan phytoalexin biosynthesis in elicitor-challenged chickpea (*Cicer arietinum* L.) cell cultures: purification, characterization and cDNA cloning of NADPH: isoflavone oxidoreductase," *Eur J Biochem* 200:751–757 (1991).

Wiermann, R., "Secondary plant products and cell and tissue differentiation," In *The Biochemistry of Plants*, P.K. Stumpf and E.E. Conn, eds., New York, Academic Press, 7:85–116 (1981).

Yu, et al., "Purification and biochemical characterization of proteins which bind to the H-box cis-element implicated in transcriptional activation of plant defense genes," *Plant J* 3:805–816 (1993).

Oomen et al. 1992. J. Cell. Biochem. Suppl. 16F:220 Oommen.

| | |
|---|---|
| 1 | <u>ACTAGT</u>TTTGTAAGAATTTTTTGAAACTTGTGTAATCCAATATTAAAAAA |
| | SpeI |
| 51 | TGTAAAAAAAATGTTATCTTTTATACAAAACTTACCTTTTATGTTTCTT |
| 101 | TAACTAATGCCTTAAAGATACCGATTAACATCCAATAATTAAATACCACC |
| 151 | TAACATCAACAATTACAAGAAATAACAACCTATTGAAACTCATTGCAAA |
| 201 | CGCTCTAACTTGCAAACTTTCTTTTGAGAAAGTATTTTTATTTAACTTT |
| 251 | CTAGGTGTTGAAGAACAATTTATGTTGAGTGAATATTAAACACATTTTT |
| 301 | TATAATAGTTGAATCTATCAAATGAAGAC<u>GAATTC</u>AACATGCAGGTTGGG |
| | EcoRI |
| 351 | TTGTGTCATTGTTAAAAAGTTGTGAAGTAAAGGTTTCAAGTTGAATATTT |
| 401 | AAAAAATCCTTAAAAAAGTTATATGTATATATCATGTTAATAATAATAAT |
| 451 | TAGTATAAATCGGTGTATTCTTTTGTTCTCTTTGCTAAGATATATTCTTG |
| 501 | CTTCCGGCCAAGTTTTCAGCAGAATTGTTTGATAAGTAGAGTTTTTTTAT |
| 551 | ATATATTTTAACTGACTACTAATATGTTTTATACGGAGTTAATTAAGTAG |
| 601 | ACTTAAGAGAAGGCGTCAATTTTGACCAACAGGGCTGCTTCTATTTCAAC |
| 651 | AACAATGAATATTAAATTTGGTCACTAAAACACACAGAGAGTAGTAGATG |
| 701 | GATTGAAGTTGGTGGCAATCCAAGTTTGTCC<u>TATAAAT</u>ATCAAACAAAGT |
| 751 | ATAGCTATTCATCACACACTCACTACTACTTTGGTAACGTATTCAAAACA |
| 801 | AGAAAAAACAGACAAAAACATAAACACACTTGTTTTTTT<u>ACTAGT</u>TATTT |
| | SpeI |
| 851 | TTTTCCAATGGCAACTGAAAACAAAATCCTGATCCTAGGACCAACAGGAG |
| |    M  A  T  E  N  K  I  L  I  L  G  P  T  G  A |
| 901 | CTATTGGAAGACACATAGTTTGGGCAAGTATTAAAGCAGGAAATCCAACA |
| |  I  G  R  H  I  V  W  A  S  I  K  A  G  N  P  T |
| 951 | TATGCTTTGGTTAGAAAAACACCTGGCAATGTTAACAAGCCAAAGCTTAT |
| |  Y  A  L  V  R  K  T  P  G  N  V  N  K  P  K  L  I |
| 1001 | TACAGCTGCTAATCCTGAAACCAAGGAAGAGCTTATTGATAATTACCAAT |
| |  T  A  A  N  P  E  T  K  E  E  L  I  D  N  Y  Q  S |
| 1051 | CTTTAGGAGTTATTCTACTTGAAgtaagtgatttcaatatgtgaataat |
| |  L  G  V  I  L  L  E |
| 1101 | tttatattctatatatttattaaattgacctaatcaatatgtctttgact |
| 1151 | ctgcagGGTGATATAAATGATCATGAAACTCTTGTTAAGGCAATCAAGCA |
| |     G  D  I  N  D  H  E  T  L  V  K  A  I  K  Q |

Fig. 1a

```
1201  AGTTGACATTGTGATCTGTGCTGCTGGTAGACTACTAATTGAAGATCAGG
       V  D  I  V  I  C  A  A  G  R  L  L  I  E  D  Q  V
1251  TCAAGATTATTAAAGCAATTAAAGAAGCTGGAAACGTTAAGgtgaacaaa
       K  I  I  K  A  I  K  E  A  G  N  V  K
1301  tttgtcactacaccagtaaataagtccaaataagtcaattcatatagagt
1351  cttagttagtaataactctttgatggttagatttgtactcgttatattga
1401  atagtggtactaaatttcttgtgtcgacagAAATTTTTCCCATCTGAATT
                                     K  F  F  P  S  E  F
1451  TGGGCTAGACGTGGACCGTCATGAGGCCGTTGAGCCAGTTAGACAAGTTT
       G  L  D  V  D  R  H  E  A  V  E  P  V  R  Q  V  F
1501  TTGAAGAAAAAGCAAGTATCCGAAGAGTAATTGAAGCCGAAGGAGTTCCT
       E  E  K  A  S  I  R  R  V  I  E  A  E  G  V  P
1551  TACACTTACCTTTGTTGCCACGCCTTTACCGGTTACTTCTTACGTAACTT
       Y  T  Y  L  C  C  H  A  F  T  G  Y  F  L  R  N  L
1601  GGCTCAACTCGACACAACTGATCCTCCTCGGGACAAAGTTGTCATTCTTG
       A  Q  L  D  T  T  D  P  P  R  D  K  V  V  I  L  G
1651  GAGATGGAAATGTGAAAGgtaacagacttagtcacagaacaattcaacaa
       D  G  N  V  K  G
1701  actagtattgaacaaaagacacacaattcagttgtttcaataattatacc
1751  ttactcatttcagGAGCATATGTAACTGAGGCTGATGTGGGAACTTTTAC
                    A  Y  V  T  E  A  D  V  G  T  F  T
1801  CATTAGAGCAGCAAATGATCCCAACACATTGAACAAAGCTGTCCATATTA
       I  R  A  A  N  D  P  N  T  L  N  K  A  V  H  I  R
1851  GACTCCCCGAAAATTATTTGACCCAAAATGAGGTCATTGCCCTTTGGGAG
       L  P  E  N  Y  L  T  Q  N  E  V  I  A  L  W  E
1901  AAAAAGATTGGGAAGACTCTTGAGAAAACTTATGTTTCAGAGGAACAAGT
       K  K  I  G  K  T  L  E  K  T  Y  V  S  E  E  Q  V
1951  TCTCAAGGATATTCAAGgtcagtaaaataaacgctttataaatattgtta
       L  K  D  I  Q  E
2001  agaatttttacaccggtaatcaatcatagttgataaatcgttaaaaatat
2051  ttgattttaattatatctatttaatgaccgcacaaatatctgacggtgt
2101  atcaaaattaatctcttagtgttaaattatgagtgacatgtatgtcattt
2151  tacagcaattttgtaaaattaatcatgaaatatgttacttgctatgcagA
```

Fig. 1b

```
2201  ATCTTCATTCCCTCATAACTATTTGTTGGCATTGTACCATTCACAACAAA
        S  S  F  P  H  N  Y  L  L  A  L  Y  H  S  Q  Q  I
2251  TAAAAGGAGATGCAGTGTATGAGATTGATCCAGCCAAAGATATTGAAGCT
         K  G  D  A  V  Y  E  I  D  P  A  K  D  I  E  A
2301  TCTGAAGCCTATCCAGATGTGACATACACCACTGCTGATGAATATTTGAA
        S  E  A  Y  P  D  V  T  Y  T  T  A  D  E  Y  L  N
2351  TCAATTTGTCTAACGAATGCTAAGGAAATGTTCAATAAGACAATGAATTT
         Q  F  V  -
2401  AAAAAAAAAAAAGTTTCACATCTGTGTATGTTTCTTGTGTTTGTTTAGTT
2451  TTGTTCTCAGTAATCCCTCCCAATTGATGTAATAATTTACAAAAATAATA
2501  AATATTATATTCTGTTCCACTGTTTGCACATCTTTGTCTCTTTGTTCAAT
```

```
2551  ATTTTACATTGTGGCTTCTCATTTTATGCGTCACTGTGAAGGGCCGACTC
2601  CAAAATAATTAAACGCACGCCCAAAATGGACTGAAAAATTCACTAATTA
2651  GACAAGTAGAAATATAATAAGAACTGAAATAATGACGAAAAAAAATAAG
2701  AACTAAAAAAATAGAAATATTAGGAATTC 2730
                                 EcoRI
```

Fig. 1c

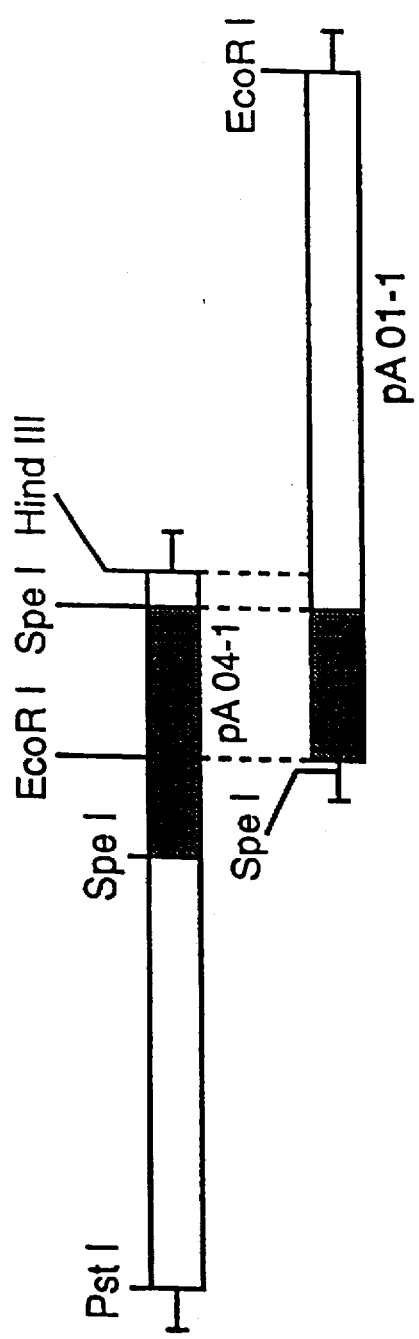
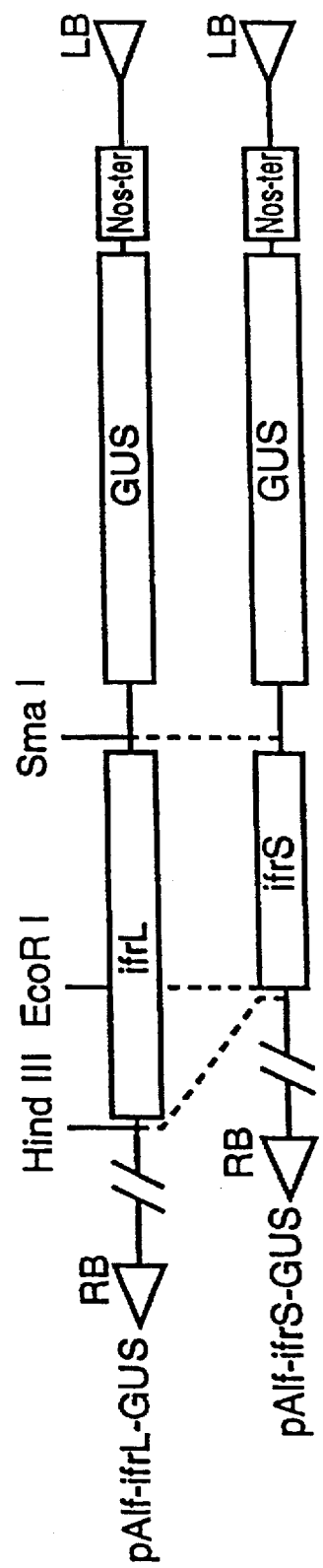
Fig. 2a
Fig. 2b

ISOFLAVONE REDUCTASE PROMOTER

TECHNICAL FIELD

This invention relates to gene promoters and their use in directing transcription of structural transgenes.

BACKGROUND OF THE INVENTION

Recombinant DNA technology and genetic engineering have made it possible to introduce desired DNA sequences or genes into cells to allow for the expression of proteins of interest. This technology has been applied in plants to provide plants having unique characteristics. In order to obtain adequate expression of a gene inserted into a plant cell, a promoter sequence operable in plant cells is often required. Promoters are typically untranslated regions upstream from the coding region. They can have various features and regulatory functions but are generally involved in the binding of RNA polymerase to initiate transcription.

Although a gene coding for a protein of interest may be available, frequently its promoter will not drive expression in the plant tissues as desired. Additionally, if the gene of interest has been obtained as cDNA, it will not have a promoter. For these reasons, structural genes or antisense sequences are often fused to a promoter isolated from some other gene which may originally have come from the same organism or an entirely different one. Such a promoter is chosen according to its pattern of expression.

Often, a promoter which is constitutive in the plant to be transformed is required; that is, a promoter which is always driving the expression of the transgene is needed. The 35S promoter of cauliflower mosaic virus (CaMV35S) is one example of a well known promoter which is constitutive in most plant tissues. In other circumstances, an inducible promoter will be fused to the gene. Such a promoter directs very low levels of transcription or none at all until it is induced by a chemical inducing agent, a change in temperature or some other factor.

At other times, a promoter which has a particular developmental pattern of expression is needed. In that case, a promoter capable of directing expression only in the desired tissue must be chosen, because while a gene or antisense sequence introduced into a plant may be of great benefit when expressed at an appropriate tissue location and time, the protein it encodes may be unneeded or even detrimental when present in other tissues or at different times. For example, if a gene was introduced to affect seed oils, a seed specific promoter would be required. Such tissue specific promoters may be constitutive or inducible.

Some promoters have already been characterized, including promoters of genes coding for enzymes involved early in the phytoalexin biosynthetic pathway. Phytoalexins are low molecular weight antimicrobial compounds synthesized by plants in response to attempted infection by fungal pathogens or exposure to elicitor macromolecules. (Dixon, et al., "Phytoalexins: enzymology and molecular biology," *Adv Enzymol Related Areas Mol Biol* 55:1–135 (1983)).

Genes encoding early enzymes in the phytoalexin biosynthetic pathway, such as phenylalanine ammonia-lyase (PAL) and chalcone synthase (CHS), have been cloned from several plant species, and their developmental and environmental expression patterns studied using promoter-reporter gene fusions. (Liang, et al., "Developmental and environmental regulation of a phenylalanine ammonia-lyase-α-glucuronidase gene fusion in transgenic tobacco plants," *Proc Natl Acad Sci USA* 86:9284–9288 (1989); Stermer, et al., "Infection and stress activation of bean chalcone synthase promoters in transgenic tobacco," *Mol Plant-Microbe Interact* 3:381–388 (1990); Ohl, et al., "Functional properties of a phenylalanine ammonia-lyase promoter from Arabidopsis," *Plant Cell* 2:837–848 (1990); Fritze, et al., "Developmental and UV light regulation of the snapdragon chalcone synthase promoter," *Plant Cell* 3:893–905 (1991)). The complex expression patterns of these genes are consistent with the involvement of the corresponding enzymes in the synthesis of a wide range of functionally distinct phenylpropanoid-derived secondary products. The promoters of several PAL and CHS genes share common regulatory cis-elements, consistent with the coordinated transcriptional activation of these genes at the onset of the isoflavonoid phytoalexin response.

Enzymes specific to isoflavonoid phytoalexin biosynthesis have recently been characterized from several members of the leguminosae. In alfalfa, isoflavone reductase (IFR, E.C. 1.3.1.45) catalyzes the NADPH-dependent reduction of 2'-hydroxyformononetin to vestitone, the penultimate step in the synthesis of medicarpin. Subsequent reduction and ring closure convert vestitone to medicarpin. IFR has been purified and characterized from several legumes and IFR cDNA clones obtained from alfalfa (Paiva, et al., *Plant Mol Biol* 17:653–667 (1991)), chickpea (Tiemann, et al., "Pterocarpan phytoalexin biosynthesis in elicitor-challenged chickpea (*Cicer arietinum* L.) cell cultures: Purification, characterization and cDNA cloning of NADPH: isoflavone oxidoreductase" *Eur J Biochem* 200:751–757 (1991)) and pea (Paiva et al., *Archives of Biochemistry & Biophysics* 312:501–510 (1994)). In unstressed alfalfa plants, transcripts from the single alfalfa IFR gene are detected mainly in roots and root nodules, consistent with the accumulation of a medicarpin conjugate, medicarpin-3-O-glucoside-6"-O-malonate (MGM) only in these organs. (Paiva, et al., *Plant Mol Biol* 17:653–667 (1991)). IFR transcript accumulation is, however, strongly induced in infected leaves or elicited cell cultures at the onset of medicarpin accumulation. Thus, the levels of IFR transcript in these tissues are elevated.

The IFR promoter has now been isolated and modified for use in driving the expression of genes or DNA sequences operably linked to it. The transcription of sequences which would be useful in plants can be controlled according to the patterns of expression displayed by the IFR promoter and portions thereof in a given transformed plant tissue or species. The IFR promoter helps meet the continuing need for promoters with characteristics which will provide more flexibility, specificity and uniqueness to expression of desired genes in order to advance the field of recombinant plant genetics and to provide increased utilities for introduced genes.

SUMMARY OF THE INVENTION

New promoters derived from the isoflavone reductase gene upstream activating region are provided. These promoters are capable of directing the transcription of structural genes other than an IFR gene in legumes and other plants. The characteristics of expression depend on which of the IFR-derived promoters are used, the plant tissue and the need or presence of an inducing agent.

The invention is also directed to a vector nucleic acid comprising IFR-derived promoters in a transcriptionally functional relationship with a structural gene foreign to it.

The invention further comprises plant cells transformed with the IFR-derived promoters in a transcriptionally functional relationship to a structural gene.

The invention also comprises a method of expressing a structural gene under the control of an IFR-derived promoter.

These and other features, aspects and advantages of the present invention will become better understood with reference to the following description and appended claims.

BRIEF DESCRIPTION OF THE DRAWINGS

FIG. 1a–FIG. 1c depict the nucleotide sequence of the alfalfa IFR gene. The sequence of the promoter, 5' and 3' untranslated regions, and exons are in uppercase letters. Introns are indicated in lowercase letters. The deduced amino acid sequence is shown in single-letter code below the exon sequences; the transcription initiation site as determined by primer extension is marked with an arrow (position 766); the possible TATA box (position 732 to 738) and polyadenylation signals (position 2481 to 2486 and 2494 to 2502) are underlined; the polyadenylation site is marked with an arrow (position 2518); and the restriction sites used in the generation of promoter-GUS fusions: EcoRI at position 330 to 335 and SpeI at positions 1 to 6 and 840 to 845 along with the EcoRI site at position 2725 to 2730 that span the 2.4 kb EcoRI fragment of pAO1-1, are underlined and respectively labeled underneath as either EcoRI or SpeI.

FIG. 2a depicts restriction maps of the overlapping subclones pAO1-1 and pAO4-1 from which promoter sequences were isolated. The shaded area in both clones represent the promoter sequences that were excised by SpeI digestion.

FIG. 2b depicts restriction maps of the relevant portions of the T-DNA portions of the binary vectors pAlf-ifrL-GUS and pAlf-ifrS-GUS. RB, right border; LB, left border; Nos term, nopaline synthase terminator sequence.

DETAILED DESCRIPTION

Figure 3A:
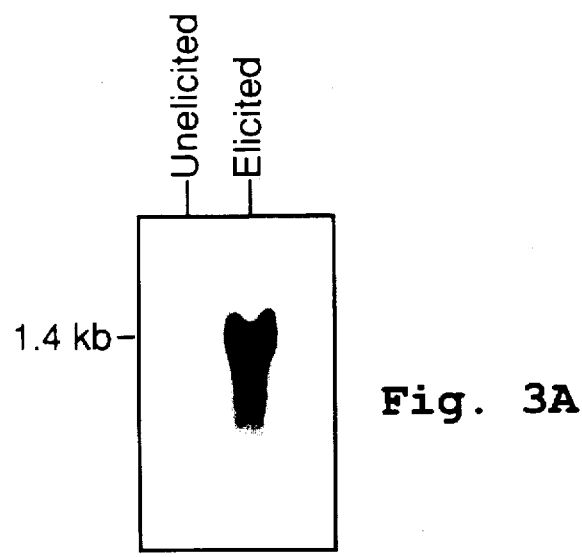
FIG. 3a is a Northern blot of RNA from unelicited and elicited alfalfa cell suspension cultures probed with a labeled internal HindIII fragment (containing coding sequences for IFR) of pAO1-1. RNA was isolated from cell cultures that were exposed to yeast elicitor for 3 hours.

The following description provides details of the manner in which the embodiments of the present invention may be made and used in order to control the expression of transgenes in plants in a way not previously known.

The IFR promoter has now been isolated and characterized as to its developmental and elicitor/infection-induced expression in transgenic alfalfa, and in tobacco, a species which lacks the isoflavonoid pathway. As used herein, the term promoter includes all promoter elements, such as, but not limited to, TATA boxes, GC boxes and CCAAT boxes as well as transcriptional control elements including enhancers. Promoter is synonymous with upstream activating region. As IFR is specific for the synthesis of defense-related isoflavonoid compounds, the IFR gene promoter may respond to a more limited set of signals than do PAL and CHS gene promoters. Thus, an IFR-derived promoter will be useful for driving expression of antimicrobial proteins or biosynthetic enzymes in transgenic plants.

The present invention involves the isolation, modification and characterization of the IFR promoter as well as its use to control expression of genes in transformed plants. The plants to which the invention can be applied include the commercially important forage legumes such as, but not limited to, alfalfa and large-seeded legumes (grain legumes) such as soybeans, beans and peas. IFR-derived promoters are also useful in plants which lack the isoflavonoid pathway as powerful constitutive promoters for the whole plant or to control expression in certain tissues.

In line with the observed patterns of expression, the invention includes the use of IFR-derived promoters fused to a sequence of DNA to be expressed according to the developmental and stress-induced expression the specific promoter directs. In a preferred embodiment, both an approximately 765 base pair and shorter regions of the IFR promoter can be used to drive root-specific constitutive expression as well as elicitor-induced expression in other tissues of legumes. Both the 765 base pair and the shorter promoters have been found to confer stronger expression in elicitor-induced cell cultures of alfalfa than does the commonly used 35S promoter.

In another preferred embodiment of the invention, the IFR-derived promoters can be used for constitutive expression of genes when used in heterologous species such as tobacco. The approximately 765 base pair promoter (approximately position 1 to 765 of SEQ ID NO:1) has been shown to confer strong expression in cell cultures of the genes to which it is fused. This promoter can be longer or shorter, but at least a portion of the 329 bp region on the 5' end is required for full constitutive control. Promoters which drive high levels of constitutive expression continue to be of benefit in the field of plant genetics. In another embodiment, at least a portion of an approximately 436 base pair region of the promoter (approximately position 330 to 765 of SEQ ID NO:1) can be used to drive constitutive expression of transgenes in pollen, fruits and seeds of heterologous species. This embodiment also allows inducible expression in the remaining tissues.

In another embodiment, an IFR-derived promoter can be fused to a reporter type gene which can serve as an early indicator of plant infection. In yet another embodiment, the promoter can also be useful in screening for substances or conditions which induce defense reactions, and in still another embodiment, it may be possible to delete or alter portions of the IFR promoter to eliminate the constitutive root expression while retaining localized pathogen inducibility as was achieved for the tobacco TobRB7 promoter. (Opperman, et al., "Root-knot nematode—directed expression of a plant root-specific gene," *Science* 263:221–223 (1994)). Such a pathogen-specific promoter would be valuable for defense strategies which kill both the pathogen and a few host cells by the localized production of the highly toxic product.

According to the present invention, there is provided the DNA insert as contained in vectors pAO4-1 and pAO1-1, and any variants that are the functional equivalents thereof. It is expected that additions or deletions can be made to either the 5' or 3' ends of both promoter fragments without altering their activity, which activity can be tested by the methodology of Examples 1–4.

The source of the promoters of this invention can be the genomic DNA library of a plant which has the isoflavonoid pathway, according to the procedures taught in this Application or by polymerase chain reaction (PCR) using genomic DNA of such a plant as template. They can be synthesized from the appropriate bases using, for example, FIG. 1a–FIG. 1c or SEQ ID NO:1 as a guide, or arrived at by any of several other ways known in the art. The DNA can be then cloned into a vector, in a position upstream from the coding region of a gene of interest. The sequence to be expressed may be in the sense or antisense orientation. The construct in a suitable expression vector may then be used to transform plants as desired, to make the plants of this invention. Transformation may be accomplished by any known means including Agrobacterium, biolistic process or electroporation. Transformed plants may be regenerated by standard protocols well known to those with average skill in the art, such as organogenesis from leaf discs or somatic embryogenesis. The transformed plants may be propagated sexually, or by cell or tissue culture.

EXAMPLE 1

Isolation and Characterization of the Alfalfa Isoflavone Reductase Gene

A genomic library of *Medicago sativa* cv. Apollo (constructed by G. Gowri & B. Shorrosh, Noble Foundation) in the λFix II system (Stratagene, La Jolla, Calif.) was screened using as a probe the 0.75 kb internal HindIII fragment of pIFRalf1. (Paiva et al., *Plant Mol Biol* 17:653–667 (1991)). Hybridization and washing conditions were as recommended in the manual (Preferred Method) supplied with the Colony/Plaque Screen hybridization transfer membranes (DuPont, Boston, Mass.) except that 6×SSPE replaced 1M NaCl in the hybridizations and SSPE replaced SSC in the washes following hybridizations. Positive clones from the first round of screening were purified by two additional rounds of screening. Restriction mapping and Southern blot hybridization with four positive clones revealed strongly hybridizing 2.4 kb EcoRI and 1.4 kb HindIII fragments in each case, similar to the pattern observed in Southern blot analysis of total alfalfa genomic DNA. (Paiva et al., *Plant Mol Biol* 17:653–667 (1991)). The hybridizing 2.4 kb EcoRI fragment from one phage clone was subcloned into pBluescript II SK- and designated pAO1-1. Sequence analysis revealed that this clone contained the entire coding region of IFR, but only 528 bp 5' to the open reading frame (ORF). A 5' end-specific probe (XbaI/HindIII fragment of pIFRalf1) was used to identify an overlapping 4 kb HindIII fragment which was also subcloned into pBluescript II SK-. A 2 kb PstI fragment was removed from the 5' end to produce pAO4-1. The complete nucleotide sequence of pAO1-1 (EcoRI to EcoRI site) and additional 5' flanking promoter sequence from pAO4-1 (329 bp; SpeI to EcoRI) are shown in FIG. 1a–FIG. 1c. The positions of four introns were deduced by comparison with the cDNA sequence of pIFRalf1. The splice points conform to the "GT-AG" rule for donor and acceptor sites. (Breathnach, U. and Chambon, P. "Organization and expression of eukaryotic split genes coding for proteins," *Annu Rev Biochem* 50:349–383 (1981)). The deduced coding regions of pAO1-1 and the cDNA pIFRalf1 were 98.1% identical at the nucleotide level and 99.1% identical at the amino acid level, with only one functionally different amino acid substitution.

The start of transcription was mapped by primer extension analysis to 92 nucleotides from the start of translation. A synthetic 22-mer oligonucleotide complementary to the N-terminal end of the IFR coding region (positions 858 to 879) was end-labeled with T4 polynucleotide kinase and γ-[$^{32}$P]ATP. Up to $5 \times 10^4$ cpm of labeled primer was annealed to 10 μg of total RNA in a 20 μl reaction containing 100 mM Tris-HCl, pH 8.3, 140 mM KCl, 10 mM MgCl2, 20 mM β-mercaptoethanol, 1 mM dNTPs, and 40 units of RNasin (Promega, Madison, Wis.). (Pfitzner, et al., "DNA sequence analysis of a PR-1a gene from tobacco: Molecular relationship of heat shock and pathogen responses in plants," *Mol Gen Genet* 211:290–295 (1988)). The reaction was carried out in the presence of 200 units of reverse transcriptase (Superscript, BRL, Gaithersburg, Md.) at 42° C. for 45 min. The products of the primer extension reaction were analyzed on a 6% polyacrylamide gel containing 8M urea along with a sequencing reaction done on pAO1-1 with the same primer. Sequencing for the primer extension reaction was done using Sequenase (United States Biochemicals, Cleveland, Ohio) according to the instructions provided by the vendor. Transcripts from elicited and unelicited alfalfa suspension cells together with transcripts from alfalfa roots gave the same major primer extension product. In elicited cells, a minor reverse transcription product two nucleotides longer was also observed, probably indicating a second start of transcription from the next available site. A "TATA" box is located 34 nucleotides upstream from the transcription start site, and two possible "CAAT box" elements are located at positions 615 (GTCAATTT) and 653 (CAAT).

The 765 bp of available IFR promoter sequence was searched for sequences similar to previously identified cis-elements functional in stress-induced or developmentally-regulated expression of plant defense genes. It was found that regions of IFR have some similarities to Box P; however, there are substantial differences as well. Best matches were for near complete (position 146) and partial (position 626) elements homologous to the Box P region identified as important for elicitor-responsiveness of a parsley PAL promoter. (Lois, et al., "A phenylalanine ammonia-lyase gene from parsley: structure, regulation and identification of elicitor and light responsive cis-acting elements," *EMBO J* 8:1641–1648 (1989)). Box P binds an elicitor-inducible B-ZIP transcription factor termed BPF-1 (da Costa e Silva, et al., "BPF-1, a pathogen-induced DNA-binding protein involved in the plant defense response," *Plant J* 4:125–135 (1993)). Related sequences are also present in bean PAL and CHS genes (Dixon, R. A. and Harrison, M. J., "Activation, structure and organization of genes involved in microbial defense in plants," *Adv Genetics* 28:165–234 (1990)) and in the alfalfa CHS2 gene (N. L. Paiva, H. Junghans, R. A. Gonzales and R. A. Dixon, unpublished results). Other important elements such as the H-box, G-box and SBF-1 binding sites which have been implicated in elicitor-mediated and developmental expression of bean CHS genes (Harrison, et al., "Characterization of a nuclear protein that binds to three elements within the silencer region of a bean chalcone synthase gene promoter," *Proc Natl Acad Sci USA* 88:2515–2519 (1991); Loake, et al., "Combination of H-box [CCTACC(N)$_7$CT] and G-box (CACGTG) cis elements is necessary for feedforward stimulation of a chalcone synthase promoter by the phenylpropanoid-pathway intermediate p-coumaric acid," *Proc Natl Acad Sci USA* 89:9230–9234 (1992); and Yu, et al., "Purification and biochemical characterization of proteins which bind to the H-box cis-element implicated in transcriptional activation of plant defense genes," *Plant J* 3:805–816 (1993)) were not present in the IFR upstream region.

EXAMPLE 2

Alfalfa IFR Promoter-GUS Fusions in Transgenic Plants

The following example describes the fusion of IFR-derived promoters to a reporter gene so that the characteristics of the promoters may be determined. To use the promoters to control the expression of other genes, a similar procedure should be followed with modifications which will occur to one skilled in the art depending on factors such as the restriction sites available in the sequence of the gene of interest.

Promoter sequences derived from the alfalfa IFR gene were fused to the β-glucuronidase gene in the binary vector pBI101.1 (Jefferson, et al., "GUS fusions: β-Glucuronidase as a sensitive and versatile gene fusion marker in higher plants," *EMBO J* 6:3901–3907 (1987)) as outlined in FIG. 2. Plasmids pAO1-1 and pAO4-1 contain overlapping regions of the IFR genomic clone. Digestion of the plasmid pAO1-1 yielded a 540 bp SpeI fragment containing 436 bp of the promoter region and 80 bp of the 5' untranslated region (EcoRI to SpeI site), along with 24 bases of the vector's multiple cloning site. Digestion of pAO4-1 yielded a 845 bp SpeI fragment containing an additional 329 bp of upstream promoter sequence. These two SpeI fragments were ligated into the XbaI site of pBI101.1 (Jefferson, et al., *EMBO J* 6:3901–3907 (1987)) to generate pAlf-ifrS-GUS and pAlf-ifrL-GUS, respectively. The two binary vectors were maintained in the *E. coli* strain DH5α u and then transferred to *Agrobacterium tumefaciens* strain LBA4404 by direct DNA transfer. (An, G., "Binary Ti vectors for plant transformation and promoter analysis," *Methods Enzymol* 153:292–305 (1987)). Transgenic plants transformed with the construct pAlf-ifrL-GUS, containing the longer (765 bp) promoter fragment, are referred to as "ifrL-GUS" plants. Similarly, transgenic plants transformed with pAlf-ifrS-GUS, containing the shorter promoter fragment (a 329 bp deletion to the EcoRI site within the longer promoter), are referred to as "ifrS-GUS" plants. Both constructs are transcriptional fusions to the GUS gene in which 80 nucleotides of the 92 nucleotide untranslated leader sequence of the IFR transcript were maintained intact. These two constructs, along with pBI121 (CaMV 35S promoter-GUS for constitutive expression controls) and pBI101.1 (as a control for GUS with no promoter) were introduced into tobacco and alfalfa plants by Agrobacterium-mediated plant transformation. Regenerated plants were shown to be transformed by Southern analysis using both a GUS-specific probe (BamHI/SacI fragment of pBI101.1) and an IFR-promoter-specific probe (the 845 bp SpeI fragment from pAO4-1). Border analysis indicated a range of 1 to 6 transgene copies in tobacco and 1 to 4 copies in alfalfa.

Of eight ifrL-GUS independent tobacco transformants with the same qualitative GUS staining pattern, four plants (T8, T9, T11 and T14) showed higher levels of staining with X-gluc and were used in all studies. All seven independent transgenic tobacco plants obtained by transformation with the short promoter construct showed the same staining pattern as described below. In the case of alfalfa, all transgenic plants obtained by transformation with the long or short promoter constructs showed the same staining pattern. Three independent transformants that showed strong staining were selected to represent each promoter construct (A3, A4 and A7 for the long promoter and A8, A9 and A11 for the short promoter).

EXAMPLE 3

Plant Transformation and Regeneration

Tobacco and alfalfa plants were transformed with *A. tumefaciens* strain LBA4404 harboring the gene construct of interest by leaf disc methods. Transgenic tobacco plants (*Nicotiana tabacum* cv. Xanthi NF) were generated as described before (Rogers, et al., "Gene transfer in plants: Production of transformed plants using Ti plasmid vectors," *Methods Enzymol* 118:627–640 (1986)), with regeneration under kanamycin selection. Transgenic alfalfa plants were generated from the transformation and regeneration of competent alfalfa cultivar Regen SY (Bingham, E. T., "Registration of alfalfa hybrid Regen-SY germplasm for tissue culture and transformation research," *Crop Sci* 31:1098 (1991)), following a modified version of published procedures (Bingham, et al., "Breeding alfalfa which regenerates from callus tissue in culture," *Crop Sci* 15:719–721 (1975)). Briefly, leaf discs from young trifoliate leaves were inoculated with a suspension of Agrobacterium harboring the binary construct and incubated on solid B5h plates (Brown, O. C. W. and Atanassov, A., "Role of genetic background in somatic embryogenesis in Medicago," *Plant Cell Tiss Organ Cult* 4:111–122 (1985)) for four days (16 hours light at 24° C.). The explants were then washed twice with water to remove bacteria and incubated for four more days on new B5h plates. Explants were then washed twice with water and transferred to selection plates (B5h plates with 100 mg/L timentin (Smith-Kline Beecham, Philadelphia, Pa.) and 25 mg/L kanamycin (Sigma, St. Louis, Mo.)). Calli and occasional embryos appeared after two weeks and were transferred to new selection plates, making sure the calli were spread out. Plants were incubated for another week to allow development of additional embryos. The calli and embryos were then transferred to B5 plates (no hormones, but with antibiotics as before). After two weeks, the calli and embryos were transferred to fresh B5 plates (with antibiotics). After one to two weeks, individual embryos were cultured on MS plates (Murashige, T., and Skoog, F., "A revised medium for rapid growth and bioassays with tobacco tissue culture," *Physiol Plant* 15:473–497 (1962)) with antibiotics (50 mg/L timentin and 25 mg/L kanamycin); plantlets were formed within one to three weeks, occasionally with roots. These were transferred to plastic boxes (Magenta Corp, Chicago, Ill.) with MS agar media and antibiotics. Plants were maintained on MS media with antibiotics and propagated by cutting. Plants were also transferred to soil in the greenhouse.

EXAMPLE 4

Characterization of IFR Promoter Activity

Plant Material

Two cultivars of alfalfa were used in this study, *Medicago sativa* cv. Apollo (AgriPro, Mission, Kans.) and cv Regen SY. (Bingham, E. T., *Crop Sci* 31:1098 (1991)). For good vegetative growth and induction of flowering, alfalfa plants were maintained at 18h/25° C. day and 6h/19° C. night cycles at approximately 70% relative humidity in controlled environmental chambers (Conviron, Asheville, N.C.). Tobacco plants were maintained in the greenhouse at 16h/25° C. day and 8h/20° C. night cycles at approximately 50% relative humidity.

Callus and cell suspension cultures of alfalfa and tobacco were generated and maintained on modified SH media as described previously (Kessmann, et al., "Stress responses in alfalfa (*Medicago sativa* L.) III. Induction of medicarpin and cytochrome P450 enzyme activities in elicitor-treated cell suspension cultures and protoplasts," *Plant Cell Rep* 9:38–41 (1990)). Yeast cell wall preparations were used to elicit cell cultures as described previously. (Paiva, et al., *Plant Mol Biol* 17:653–667 (1991)).

Nodulation and Pathogen Infection of Alfalfa

Multiple cuttings of transgenic plants were rooted in autoclaved perlite wetted with filter-sterilized nitrogen-free Hoagland's nutrient solution supplemented with trace elements. After roots form (10 days), 5 ml of a suspension of *Rhizobium meliloti* 102F51 ($OD_{600}$=0.5) was added to each cutting. Sterile water or nutrient solution was added as necessary to prevent the perlite from drying out. Nodulated roots were examined nine days, three weeks, and five weeks after inoculation.

Growth chamber (Conviron, Ashville, N.C.) grown transgenic plants were either sprayed with a spore suspension (approximately $10^5$ cfu/ml) of *Phoma medicaginis* in 0.05% Tween-20 or with dilute Tween-20 alone. Inoculated and control plants were then enclosed in clear plastic bags and grown under high humidity. Trifoliate leaves were taken at intervals of two, four and seven days and stained with X-gluc to detect GUS activity.

DNA and RNA Gel Blot Hybridization

DNA was isolated from tobacco and alfalfa plants as described. (Junghans, H., and Metzlaff, M., "A simple and rapid method for the preparation of total plant DNA," *BioTechniques* 8:176 (1990)). RNA was isolated as described in Paiva et al., *Plant Mol Biol* 17:653–667 (1991). Up to 10 µg of total RNA or genomic DNA was used in Northern or Southern blot analysis, respectively. Transfer of DNA or RNA to nylon membranes and hybridizations to specific probes were carried out as recommended in the manual (Preferred Method) supplied with Gene Screen Plus hybridization transfer membranes (DuPont, Boston, Mass.); changes to the hybridization and washing conditions were as described above for library screening. Probes were labeled to high specific activity by random primer labeling. (Feinberg, A. P., and Vogelstein, B., "A technique for radiolabeling DNA restriction endonuclease fragments to a high specific activity," *Anal Biochem* 137:266–267 (1984)).

DNA Sequence Analysis

DNA was sequenced by the Sanger dideoxy sequencing method. (Sanger, et al., *Proc Natl Acad Sci USA* 74:5463–5467 (1977)). A Taq DyeDeoxy Terminator Cycle Sequencing Kit (Applied Biosystems Inc., Foster City, Calif.) was used according to the manufacturer's protocol. The products were separated on a 6% polyacrylamide gel and the data processed by an ABI 373A automated DNA sequencer. All manipulations of raw data generated from the automated system were done on the PC Gene DNA analysis software (Intelligenetics, Mountain View, Calif.).

Histochemical Localization and Fluorometric Quantitation of GUS Activity

GUS activity was localized histochemically by standard protocols. (Jefferson, R. A., "Assaying chimeric genes in plants: The GUS gene fusion system," *Plant Mol Biol Rep* 5:387–405 (1987); and Martin, et al., "Non-destructive assay systems for detection of β-glucuronidase activity in higher plants," *Plant Mol Biol Rep* 10:37–46 (1992)). Typically, sectioned tissues or whole plant parts were incubated in 75 mM sodium phosphate (pH 7.5), 1–2 mM X-gluc (5-bromo-4-chloroindolyl-β-D-glucuronic acid) in 10% dimethylformamide, and 0.5% Triton X-100 for 6 to 12 hours at 37° C. The fluorescence of 4-methylumbelliferone produced by cleavage of 4-methylumbelliferyl-β-D-glucuronic acid was measured to quantitate GUS activity (Jefferson, R. A., *Plant Mol Biol Rep* 5:387–405 (1987)), which was expressed as pmoles 4-methylumbelliferone produced per min per mg of protein. Protein concentration was measured by the Bradford assay (Bradford, M. M., "A rapid and sensitive method for the quantitation of microgram quantities of protein utilizing the principle of protein-dye binding," *Anal Biochem* 72:248–254 (1976)) using the Biorad protein assay reagent.

Figure 3B:
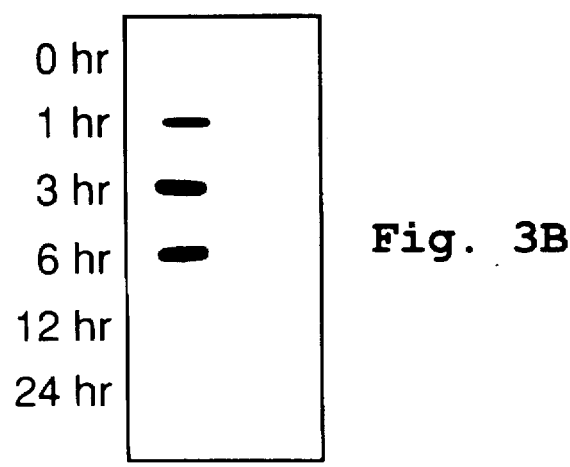
FIG. 3b is a slot blot analysis performed with immobilized cDNA specific to IFR (pIFRalf1) of run-on transcription from nuclei isolated from alfalfa cell suspension cultures treated with yeast elicitor for the times indicated.

Transcriptional Activation of Isoflavone Reductase in Response to Elicitation To ensure that the increase in IFR transcripts observed upon elicitation of alfalfa cell cultures (Paiva et al., *Plant Mol Biol* 17:653–667 (1991)) was a result of increased transcriptional activation, steady state transcript levels were determined by Northern analysis and changes in IFR transcription by run-on analysis using isolated nuclei. The nuclei were isolated from frozen elicited alfalfa cells, and run-on transcription and transcript isolation procedures carried out as described by Ni and Trelease. (Ni, W., and Trelease, R. N., "Post-transcriptional regulation of catalase isozyme expression in cotton seeds," *Plant Cell* 3:737–744 (1991)). Slot blots were prepared using Gene Screen Plus hybridization membranes with 1 µg DNA per lane; the probe consisted of the 0.75 kb HindIII fragment of pIFRalf1. The data in FIG. 3 indicate that the massive increase in IFR transcripts observed 3 hours after exposure of cells to elicitor from yeast cell walls is preceded by a striking increase in transcription rate from an undetectable initial level. Approximately equal transcription rates were observed at 3 hours and 6 hours post-elicitation, but transcription had ceased by 12 hours post-elicitation. Essentially similar transcription kinetics, with a maximum at 3 hours, were observed for PAL (data not shown).

Nuclear transcription run-on analyses have confirmed transcriptional activation of several plant defense response genes, including genes encoding the phenylpropanoid pathway enzymes PAL, 4-coumarate:CoA ligase (4-CL), CHS and chalcone isomerase (CM), in elicited cells. (Dixon and Harrison, *Adv Genet* 28:165–234 (1990)). In parsley cells, the kinetics of transcriptional activity of a range of elicitor-induced genes exhibited considerable variation, suggesting multiple mechanisms for defense gene activation. (Somssich, et al., "Differential early activation of defense-related genes in elicitor-treated parsley cells," *Plant Mol Biol* 12:227–234 (1989)). In the study to develop the present invention, the transcription kinetics of PAL, the first enzyme in the phytoalexin pathway, and IFR, the penultimate enzyme, were broadly similar, indicating that activation of PAL is not a prerequisite for induction of downstream enzymes. A detailed analysis of the very early activation kinetics (0 to 60 min) of medicarpin pathway genes has revealed nearly identical patterns for several of the genes examined, including those encoding PAL, CHS and IFR (W. Ni and R. A. Dixon, unpublished results).

Developmental Expression of IFR Promoter-GUS Fusions in Transgenic Alfalfa

Transgenic alfalfa plants were screened for observable GUS histochemical staining in roots. Both the long and the short promoter fragments conferred identical GUS expression. A zone of intense staining was seen in the region immediately behind the root tip, proximal to the quiescent center. The root cap and distal root meristematic region showed no GUS staining. Initiating lateral roots also showed high levels of GUS staining. Transverse sections through roots from both ifrL-GUS and ifrS-GUS plants revealed that GUS activity was localized exclusively to the inner cortex. This pattern of GUS expression is clearly different from that of the CaMV35S promoter in alfalfa roots, which is characterized by strongest GUS activity in the central vasculature and strong staining throughout the cortex and root tip, including the root cap. Transverse sections through stems of transgenic ifrL-GUS and ifrS-GUS alfalfa plants showed no detectable GUS activity. In comparison, transgenic plants obtained by transformation with pBI121 (35S promoter-GUS) showed staining in the vascular bundle, particularly in the secondary phloem. There was no histochemically detectable GUS activity in any shoot parts (stems, leaves, or petioles), flower parts including pollen, or seeds from ifrL-GUS or ifrS-GUS alfalfa plants, whereas pBI121-transformed plants showed intense staining in all tissues analyzed. Transformed plants containing pBI101.1 (promoterless GUS) did not show any detectable GUS activity.

Expression of IFR Promoter-GUS Fusions in Alfalfa Root Nodules

The effective *Rhizobium meliloti* strain 102F51 readily formed nodules on rooted cuttings of transgenic alfalfa. Histochemical analysis revealed a similar pattern of GUS expression in both ifrL-GUS and ifrS-GUS plants. In mature nodules (three and five weeks post-inoculation), the majority of the staining was in the proximal nodule meristem. No staining was observed in the distal meristematic region, the nodule outer cortex, or the region containing the mature, nitrogen-fixing bacteroids. In immature nodules, intense staining was observed across much of the inner, meristematic region. No staining was observed in nodules from plants transformed with pBI101.1 or from untransformed control plants.

Inducibility of IFR Promoter-GUS Fusions in Alfalfa

Transgenic ifrL-GUS and ifrS-GUS plants were inoculated with the alfalfa fungal leaf spot pathogen, *Phoma medicaginis*. Only infected leaves showed staining with X-gluc. GUS expression was very intense in a narrow zone (1 to 3 mm) around the lesions. HPLC analysis of portions of leaves similarly infected with *P. medicaginis* revealed that medicarpin accumulation is also confined to this zone. The staining intensity and pattern were identical with pathogen-infected leaves from both ifrL-GUS and ifrS-GUS plants, and strong staining was observed at two, four and seven days. Trifoliates of plants transformed with pBI101.1 did not stain after infection with *P. medicaginis*, whereas 35S-GUS plants showed decreased levels of staining on the trifoliates after pathogen infection. Wounding did not induce any observable GUS activity.

Transgenic cell suspension cultures (from callus derived from leaves of transgenic alfalfa plants) were treated with a yeast cell wall-derived elicitor which is known to induce strong accumulation of medicarpin, while matched cultures treated with water were used as controls. (Paiva et al., *Plant Mol Biol* 17:653–776 (1991)). The transgenic lines harbored the ifr-L and ifr-S promoter GUS fusions, 35S-GUS, or promoterless GUS (pBI101.1). After 17 hours of incubation under standard growth conditions, staining with X-gluc was detected only in elicitor-treated cells. Quantitative fluorescence-based GUS assay results are given in FIG. 4 as GUS activity measured as picomoles of 4-methylumbelliferone per minute per milligram of protein. The designation following the construct name indicates from which independent transgenic line the suspension was derived. T he value indicated by each bar is the average of two independent GUS enzyme assays (standard deviation$\leq \pm 7\%$. for unelicited and$\leq \pm 2\%$ for elicited cultures). The experiment was repeated with these same cell lines and additional cell lines, and similar levels of expression were obtained.

Figure 4:
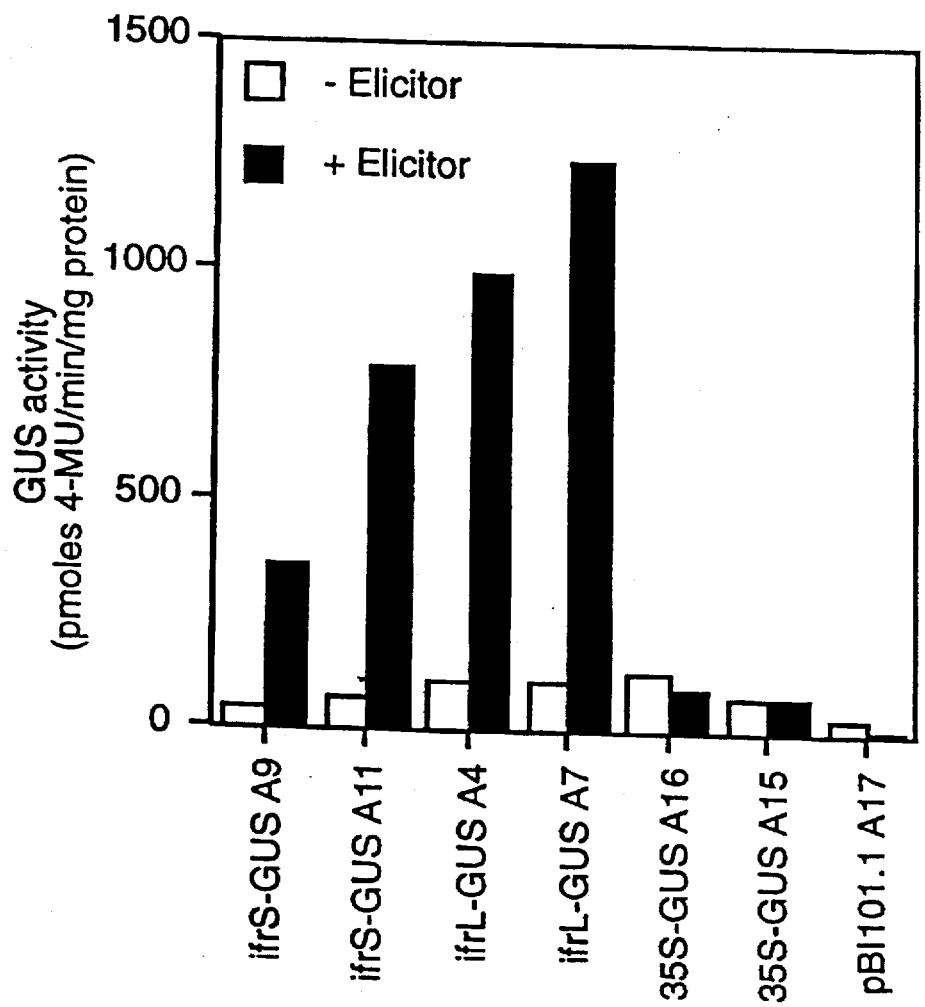
FIG. 4 is a graph depicting expression of IFR promoter-GUS fusions in cell suspension cultures derived from the transgenic alfalfa plants harboring ifr-L and ifr-S promoter GUS fusions, 35S-GUS, or promoterless GUS (pBI101.1), treated either with yeast elicitor (shaded bars) or water (white bars), and incubated under standard growth conditions for 17 hours.

As indicated in FIG. 4 an 8- to 13-fold increase in GUS activity was observed in elicited cell cultures derived from ifrS-GUS plants and a similar 10- to 12-fold induction was observed in cultures derived from ifrL-GUS plants. GUS expression in cell cultures from 35S-GUS and pBI101 transformed plants was not detectably induced by yeast elicitors. GUS activity in unelicited ifrL- and ifrS-GUS cultures was similar to that in 35S-GUS cultures; constitutive expression of the IFR promoter is expected under these conditions, as newly initiated alfalfa cell cultures constitutively accumulate significant amounts of MGM. (Kessmann, et al., "Stress responses in alfalfa (*Medicago sativa* L.) V. Constitutive and elicitor-induced accumulation of isoflavonoid conjugates in cell suspension cultures," *Plant Physiology* 94:227–232 (1990b)).

Developmental Expression of Alfalfa IFR Promoter-GUS Fusions in Transgenic Tobacco The roots of ifrL-GUS tobacco plants had a distinct pattern of X-gluc staining; the strongest staining occurred as a discrete band, excluding the distal end of the root tip. A longitudinal section through such a root showed intense staining in the proximal meristem, and high levels of expression throughout the cortex behind this zone. The root cap, the developed vascular tissue and pith together with the quiescent center and protoderm did not stain. In contrast, expression of GUS in tobacco roots controlled by the CaMV35S promoter included the root tip. Transverse sections through roots of ifrL-GUS tobacco plants showed GUS activity uniformly spanning the entire cortex, with no staining in the epidermis and the central vascular cylinder. GUS expression was not detected in the roots of tobacco plants transformed with the promotor-less GUS construct pBI101.1. In contrast to transgenic alfalfa, no GUS expression was observed in the roots of any ifrS-GUS tobacco plants.

Transverse sections through the stems of ifrL-GUS transgenic tobacco plants unexpectedly revealed GUS activity localized to the inner vascular cylinder, with parenchyma cells associated with the xylem vessels and primary xylem cells specifically being stained. The heaviest staining with X-gluc is seen through the entire central vascular cylinder in xylem, phloem and cambial cells. This is similar to the results obtained previously with the 35S promoter-GUS fusions in tobacco (Jefferson, et al., *EMBO J* 6:3901–3907 (1987)), and strongly contrasts with the expression pattern of the IFR promoter.

Strong X-gluc staining associated with the vascular system was observed in petioles of young leaves specifically in the xylem tissue that is sandwiched between two arrays of phloem. There was very little or no staining in petioles from the lower one third of the plant. Expanding leaves expressed little GUS activity; when present, most of the staining was at the leaf tips. The area close to lateral emergences such as leaves and branches showed high levels of GUS activity. The heaviest staining was seen at stem peripheries in the regions above the points of attachment of the petioles. The shoot apical meristem did not express any GUS activity, whereas the region below the meristem was expressing GUS. This contrasts with the CaMV35S promoter, which was functional throughout the entire shoot apex. Unlike the ifrL-GUS plants, GUS activity was not detected in any vegetative organ or cell of ifrS-GUS tobacco plants. Plants that were generated by transformation with pBI101.1 were also GUS-negative.

GUS activity was observed in various parts of flowers from transgenic ifrL-GUS tobacco plants. In the gynoecium of young flowers GUS activity was detected in the stigma and the placental tissue together with the base of the ovary and the flower receptacle. The style of mature, open flowers did not stain with X-gluc, but GUS activity was present in the style of flowers from all earlier stages. Ovules from different stages of unopened flowers did not stain, but occasional staining was seen in mature flowers. Whether fertilization is necessary for staining is not known, but is a possibility as cross sections through maturing fruits (formed after fertilization) showed staining of newly formed seeds. This could be developmentally controlled as there was no staining in the placental region, which had stained intensely in the mature flower. In the androecium of tobacco flowers, staining was observed in the tapetal tissue and pollen grains. Tobacco flowers from all ifrS-GUS plants showed staining in pollen, and fruits and seeds. The staining pattern is similar to that of ifrL-GUS flowers. No GUS activity was observed in the corolla of flowers of ifrL-GUS or ifrS-GUS plants. In comparison, in tobacco plants harboring the 35S promoter-GUS fusion, the entire flower expressed high levels of GUS activity, including the corolla.

Inducibility of Alfalfa IFR Promoter-GUS Fusions in Tobacco Cell Cultures

Transgenic cell suspension cultures from transgenic tobacco plants were treated with a yeast cell wall-derived elicitor which is known to induce strong accumulation of medicarpin, while matched cultures treated with water were used as controls. (Paiva et al., *Plant Mol Biol* 17:653–667 (1991)). The transgenic lines harbored the ifr-L and ifr-S promoter GUS fusions, 35S-GUS, bean CHS8-GUS, or promoterless GUS (pBI101.1). Quantitative fluorescence-based GUS assay results obtained after 17 hours of incubation under standard growth conditions are given in FIG. 5 as GUS activity measured as picomoles of 4-methylumbelliferone per minute per milligram of protein. The designation following the construct name indicates from which independent transgenic line the suspension was derived. The value indicated by each bar is the average of two independent GUS enzyme assays (standard deviation≦±4%). The experiment was repeated with these same cell lines and additional cell lines, and similar levels of expression were obtained.

Figure 5:
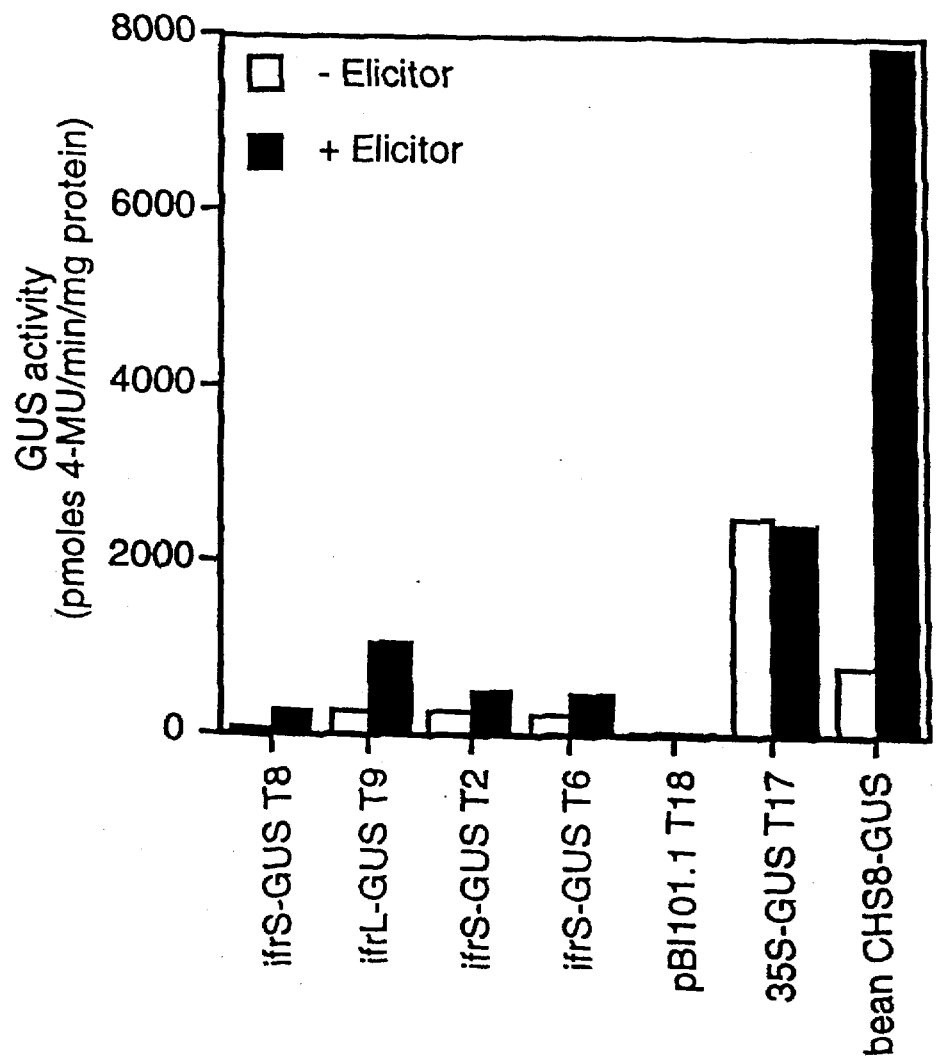
FIG. 5 is a graph depicting expression of IFR promotor-GUS fusions in cell suspension cultures derived from transgenic tobacco plants harboring ifr-L and ifr-S promoter GUS fusions, 35S-GUS, bean CHS8-GUS, and promoterless GUS (pBI101.1), treated either with yeast elicitor (shaded bars) or water (white bars), and incubated under standard growth conditions for 17 hours.

Treatment of cell suspension cultures generated from transgenic tobacco plants with yeast elicitor resulted in only a 2- to 3-fold increase in GUS activity for ifrS-GUS cell lines and a 3- to 4-fold increase in activity over unelicited cells for ifrL-GUS cell lines (FIG. 5). This was modest compared to the 10- to 12-fold increase in activity seen upon elicitation of a tobacco cell line transformed with a bean CHS8-GUS promoter construct. No consistent increase in GUS activity was detected when transgenic ifrL-GUS and ifrS-GUS tobacco plants were wounded, treated with a variety of tobacco or alfalfa fungal pathogens, infiltrated with *Pseudomonas syringae* pv syringae (successfully used to induce the CHS8 promoter in tobacco; Stermer, et al., *Mol Plant-Microbe Interact* 3:381–388 (1990)), treated with salicylic, arachidonic, or jasmonic acids (potential components of defense gene signal transduction pathways (reviewed by Lindsay et al., "Microbial recognition and activation of plant defense systems," *Trends Microbiol* 1:181–187 (1993)), or inoculated with tobacco mosaic virus (TMV) which forms local lesions on this tobacco strain.

Cis-Elements Downstream of Position 330 are Sufficient for Developmental and Elicitor-Induced Expression of the IFR Promoter in Alfalfa Northern blot analysis (Paiva et al., *Plant Mol Biol* 17:653–667 (1991)) and in situ hybridization studies have shown that IFR transcripts are constitutively expressed in nodules and root cortical cells of alfalfa plants. This correlates with the accumulation of medicarpin malonyl glycoside in root tissues, and the histochemical localization of isoflavonoid accumulation in the root cortex of legumes with similar medicarpin conjugate accumulation. (Wiermann, R., "Secondary plant products and cell and tissue differentiation," In *The Biochemistry of Plants*, P. K. Stumpf and E. E. Conn, ed. (New York: Academic Press) 7:85–116 (1981)). The absence of IFR transcripts in the aerial organs of uninfected plants likewise reflects the absence of isoflavonoid compounds in these organs. The expression patterns observed with the 765 bp and the 436 bp IFR promoter-GUS fusions in transgenic alfalfa indicate that the promoter confers correct developmental expression in the homologous species, and that root/nodule expression is determined by sequences downstream of position 330. It is not known whether the distinctive lack of GUS staining in the region distal to the root apical meristem and cell proliferation zone reflects differences in isoflavonoid metabolism in the meristematic and quiescent regions of the root tip. The bean PAL promoter exhibits strong expression in the cell proliferation zone immediately adjacent to the root apical meristem in transgenic tobacco. (Liang, et al., *Proc Natl Acad Sci USA* 86:9284–9288 (1989)). In addition, the bean CHS8 promoter (Schmid, et al., "Developmental and environmental regulation of a bean chalcone synthase promoter in transgenic tobacco," *Plant Cell* 2:619–631 (1990)) is also expressed in this zone, in the root apical meristem, and in emerging lateral roots in a manner similar to that observed for the IFR promoter. It has been suggested that phenylpropanoid/flavonoid synthesis at the root apex may produce morphogenetic signals affecting polar auxin transport or exhibiting cytokinin-like activity (Liang, et al., *Proc Natl Acad Sci USA* 86:9284–9288 (1989)) based on observations of biological activities of flavonoids (Jacobs, M., and Rubery, P. H., "Naturally occurring auxin transport regulators," *Science* 241:346–349 (1988)), and dehydrodiconiferyl glucosides (Binns, et al., "Cell division promoting activity of naturally occurring dehydrodiconiferyl glucosides: do cell wall components control cell division?" *Proc Natl Acad Sci USA* 84:980–984 (1987)), respectively. Whether isoflavonoids have morphogenetic activity, or whether their synthesis at the root tip is related to rhizosphere phenomena, remains to be determined.

Alfalfa nodules are indeterminant and maintain an active meristematic region under normal conditions. (Hirsch, et al., "Bacterial-induced changes in plant form and function," *Int J Plant Sci* 153:S171–S181 (1992)). The location of strongest GUS expression in nodules is in a tissue analogous to the strongest staining tissue in root tips, namely the proximal nodule meristem. Unlike many other legumes, alfalfa constitutively accumulates significant amounts of phytoalexin conjugates in roots and effective nodules (Paiva et al., *Plant Mol Biol* 17:653–667 (1991)). It is thought that the *Rhizobium meliloti* symbiont is either not sensitive to medicarpin (Pankhurst, C. E. and Biggs, D. R., "Sensitivity of Rhizobium to selected isoflavonoids," *Can J Microbiol* 26:542–545 (1980)) or the conjugated form, or the conjugation keeps the phytoalexin sequestered in the plant cell vacuoles away from the symbiont. We observed no evidence of promoter activity in the cells which contain the bacteroids, the actual $N_2$-fixing form of the symbiont, suggesting that phytoalexin biosynthesis is not occurring in these cells.

In transgenic alfalfa suspension cultures, the IFR promoter is strongly activated (up to 13-fold increase in GUS activity) in response to treatment with yeast elicitor, with basal expression in unelicited cells being equivalent to that of the constitutive 35S promoter. This increase in GUS activity is similar to the increase in IFR activity (10 to 12-fold) observed in elicited alfalfa cells (Paiva et al., *Plant*

*Mol Biol* 17:653–667 (1991)). As elicitor responsiveness is not lost on deletion to position 330, the putative Box P-like element between positions 146 and 157 cannot be required for reception of the elicitation stimulus. Other than an incomplete Box P core sequence (CCAACA) at position 626 and some scattered homology near position 556, there are no sequence elements common to other elicitor-induced phytoalexin biosynthetic genes in the IFR promoter downstream of position 330. This suggests that, although IFR transcription is activated simultaneously with that of other defense genes, separate signalling pathways may exist for the activation of early- and late-pathway genes in response to elicitors.

The Major Developmental Expression Pattern of the IFR Promoter in Transgenic Tobacco is Controlled by Sequences Upstream of Position 330

Tobacco does not possess the isoflavonoid branch of phenylpropanoid biosynthesis. Most previous studies in which correct developmental expression of a transgene has been reported in a heterologous species have involved promoters of genes whose products are common to both source and recipient of the transgene. (Benfey, P. N., and Chua, N. H., "Regulated genes in transgenic plants," *Science* 244:174–181 (1989)). The alfalfa IFR promoter is expressed in stem and floral tissues of tobacco according to a different developmental program from that seen in alfalfa. This difference is particularly striking in terms of the strong expression in tobacco stem and floral tissue. Although some features of this expression are similar to those of bean PAL and CHS transgenes, and tobacco IFR-like TP7 transcripts, in tobacco (Liang, et al., *Proc Natl Acad Sci USA* 86:9284–9288 (1989); Schmid, et al., *Plant Cell* 2:619–631 (1990); Drews, et al., "Regional and cell-specific gene expression patterns during petal development," *Plant Cell* 4:1383–1404 (1992)), there is a notable absence of IFR promoter expression in petal tissue. Furthermore, the elicitor-responsiveness of the promoter in transgenic tobacco cell suspensions was very poor compared to that of the bean CHS8 promoter. It is therefore possible that the IFR promoter is responsive to signals regulating the developmental programs of more than one differentially expressed endogenous tobacco gene which may or may not have defensive roles. The high constitutive expression in the aboveground parts of tobacco may also be due in part to the lack of specific negative regulatory factors in tobacco, which might normally suppress expression in these parts of alfalfa plants.

Although the 765 bp IFR promoter conferred similar patterns of GUS expression in cortical cells and root meristems of tobacco and alfalfa, the cis-elements conferring this expression are different in the two cases, as deletion to position 330 abolishes root expression in tobacco but not in alfalfa. Identification of the sequences conferring root specificity must await a detailed mutational and deletional analysis of the promoter.

During the analysis of promoters from several non-solanaceous, "nontransformable" species, investigators have relied on the use of promoter-deletion/reporter gene fusions expressed in tobacco to identify putative regulatory cis-elements (e.g., Burnett, et al., "Expression of a 3-hydroxy-3-methylglutaryl coenzyme A reductase gene from *Camptotheca acuminata* is differentially regulated by wounding and methyl jasmonate," *Plant Physiol* 103:41–48 (1993); Fritze, et al., *Plant Cell* 3:893–905 (1991); Liang, et al., *Proc Natl Acad Sci USA* 86:9284–9288 (1989); Mason, et al., "Identification of a methyl jasmonate-responsive domain in the soybean vspB promoter," *Plant Cell* 5:241–251 (1993); and Schmid, et al., *Plant Cell* 2:619–631 (1990)). Results indicate that data from such heterologous transformation experiments may be misleading. Constructs which yield ectopic expression (such as ifrL-GUS construct in stems, flowers, and seeds of the present invention) or which appear inactive in tobacco (such as ifrS-GUS construct in roots of the present invention) may exhibit correct developmental and stress-induced expression in the homologous system.

We claim:

1. An isolated DNA segment comprising a portion of the isoflavone reductase promoter region capable of directing the developmental or elicitor/infection-induced expression of a structural gene to which it is operably linked, wherein the portion of the isoflavone reductase promoter region is selected from the group consisting of about nucleotide 1 to about nucleotide 845 of the sequence depicted in SEQ ID NO: 1, about nucleotide 1 to about nucleotide 765 of the sequence depicted in SEQ ID NO: 1, about nucleotide 1 to about nucleotide 330 of the sequence depicted in SEQ ID NO: 1, about nucleotide 330 to about nucleotide 845 of the sequence depicted in SEQ ID NO: 1, and about nucleotide 330 to about nucleotide 765 of the sequence depicted in SEQ ID NO: 1.

2. The isolated DNA segment of claim 1 wherein the portion of the isoflavone reductase promoter region comprises about nucleotide 1 to about nucleotide 845 of the sequence depicted in SEQ ID NO: 1.

3. The isolated DNA segment of claim 1 wherein the portion of the isoflavone reductase promoter region comprises about nucleotide 1 to about nucleotide 765 of the sequence depicted in SEQ ID NO: 1.

4. The isolated DNA segment of claim 1 wherein the portion of the isoflavone reductase promoter region comprises about nucleotide 1 to about nucleotide 330 of the sequence depicted in SEQ ID NO: 1.

5. The isolated DNA segment of claim 1 wherein the portion of the isoflavone reductase promoter region comprises about nucleotide 330 to about nucleotide 845 of the sequence depicted in SEQ ID NO: 1.

6. The isolated DNA segment of claim 1 wherein the portion of the isoflavone reductase promoter region comprises about nucleotide 330 to about nucleotide 765 of the sequence depicted in SEQ ID NO: 1.

7. A recombinant nucleic acid molecule comprising an isolated DNA segment comprising a portion of the isoflavone reductase promoter region capable of directing the developmental or elicitor/infection induced expression of a structural gene to which it is operably linked, wherein the portion of the isoflavone reductase promoter region is selected from the group consisting of about nucleotide 1 to about nucleotide 845 of the sequence depicted in SEQ ID NO: 1, about nucleotide 1 to about nucleotide 765 of the sequence depicted in SEQ ID NO: 1, about nucleotide 1 to about nucleotide 330 of the sequence depicted in SEQ ID NO: 1, about nucleotide 330 to about nucleotide 845 of the sequence depicted in SEQ ID NO: 1, and about nucleotide 330 to about nucleotide 765 of the sequence depicted in SEQ ID NO: 1.

8. The recombinant nucleic acid molecule of claim 7 wherein the portion of the isoflavone reductase promoter region comprises about nucleotide 1 to about nucleotide 845 of the sequence depicted in SEQ ID NO: 1.

9. The recombinant nucleic acid molecule of claim 7 wherein the portion of the isoflavone reductase promoter region comprises about nucleotide 1 to about nucleotide 765 of the sequence depicted in SEQ ID NO: 1.

10. The recombinant nucleic acid molecule of claim 7 wherein the portion of the isoflavone reductase promoter region comprises about nucleotide 1 to about nucleotide 330 of the sequence depicted in SEQ ID NO: 1.

11. The recombinant nucleic acid molecule of claim 7 wherein the portion of the isoflavone reductase promoter region comprises about nucleotide 330 to about nucleotide 845 of the sequence depicted in SEQ ID NO: 1.

12. The recombinant nucleic acid molecule of claim 7 wherein the portion of the isoflavone reductase promoter region comprises about nucleotide 330 to about nucleotide 765 of the sequence depicted in SEQ ID NO: 1.

13. The recombinant nucleic acid molecule of claim 7 8, 9, 10, 11, or 12 wherein the recombinant nucleic acid molecule is a plant vector further comprising a structural gene operably linked to the portion of the isoflavone reductase promoter region.

14. The recombinant nucleic acid molecule of claim 13 wherein the plant vector is a binary vector.

15. A plant cell transformed with a recombinant nucleic acid molecule comprising an isolated DNA segment comprising a portion of the isoflavone reductase promoter region capable of directing the developmental or elicitor/infection-induced expression of an operably linked structural gene, wherein said structural gene is a gene not naturally found in the plant cell and said structural gene is operably linked to said promoter portion, wherein the portion of the isoflavone reductase promoter region is selected from the group consisting of about nucleotide 1 to about nucleotide 845 of the sequence depicted in SEQ ID NO: 1, about nucleotide 1 to about nucleotide 765 of the sequence depicted in SEQ ID NO: 1, about nucleotide 1 to about nucleotide 330 of the sequence depicted in SEQ ID NO: 1, about nucleotide 330 to about nucleotide 845 of the sequence depicted in SEQ ID NO: 1, and about nucleotide 330 to about nucleotide 765 of the sequence depicted in SEQ ID NO: 1.

16. The plant cell of claim 15 wherein the portion of the isoflavone reductase promoter region comprises about nucleotide 1 to about nucleotide 845 of the sequence depicted in SEQ ID NO: 1.

17. The plant cell of claim 15 wherein the portion of the isoflavone reductase promoter region comprises about nucleotide 1 to about nucleotide 765 of the sequence depicted in SEQ ID NO: 1.

18. The plant cell of claim 15 wherein the portion of the isoflavone reductase promoter region comprises about nucleotide 1 to about nucleotide 330 of the sequence depicted in SEQ ID NO: 1.

19. The plant cell of claim 15 wherein the portion of the isoflavone reductase promoter region comprises about nucleotide 330 to about nucleotide 845 of the sequence depicted in SEQ ID NO: 1.

20. The plant cell of claim 15 wherein the portion of the isoflavone reductase promoter region comprises about nucleotide 330 to about nucleotide 765 of the sequence depicted in SEQ ID NO: 1.

21. A plant cell transformed with a recombinant nucleic acid molecule comprising an isolated DNA segment comprising a portion of the isoflavone reductase promoter region capable of directing the developmental or elicitor/infection-induced expression of an operably linked structural gene, wherein said structural gene is a gene other than an isoflavone reductase gene and said structural gene is operably linked to said promoter portion, wherein the portion of the isoflavone reductase promoter region is selected from the group consisting of about nucleotide 1 to about nucleotide 845 of the sequence depicted in SEQ ID NO: 1, about nucleotide 1 to about nucleotide 765 of the sequence depicted in SEQ ID NO: 1, about nucleotide 1 to about nucleotide 330 in SEQ ID NO: 1, about nucleotide 330 to about nucleotide 845 of the sequence depicted in SEQ ID NO: 1, and about nucleotide 330 to about nucleotide 765 of the sequence depicted in SEQ ID NO: 1.

22. The plant cell of claim 21 wherein the portion of the isoflavone reductase promoter region comprises about nucleotide 1 to about nucleotide 845 of the sequence depicted in SEQ ID NO: 1.

23. The plant cell of claim 21 wherein the portion of the isoflavone reductase promoter region comprises about nucleotide 1 to about nucleotide 765 of the sequence depicted in SEQ ID NO: 1.

24. The plant cell of claim 21 wherein the portion of the isoflavone reductase promoter region comprises about nucleotide 1 to about nucleotide 330 of the sequence depicted in SEQ ID NO: 1.

25. The plant cell of claim 21 wherein the portion of the isoflavone reductase promoter region comprises about nucleotide 330 to about nucleotide 845 of the sequence depicted in SEQ ID NO: 1.

26. The plant cell of claim 21 wherein the portion of the isoflavone reductase promoter region comprises about nucleotide 330 to about nucleotide 765 of the sequence depicted in SEQ ID NO: 1.

27. The plant cell of claim 15, 16, 17, 18, 19, 20, 21, 22, 23, 24, 25 or 26 wherein the recombinant nucleic acid molecule is integrated into the plant chromosomal DNA.

28. A method of expressing in a plant cell a structural gene other than an isoflavone reductase gene operably linked to a DNA segment comprising a portion of the isoflavone reductase promoter region capable of directing developmental or elicitor/infection-induced expression, said method comprising:

(a) inserting the structural gene other than an isoflavone reductase gene into a vector suitable for transforming plant cells so that the structural gene is operably linked to the DNA segment comprising a portion of the isoflavone reductase promoter region capable of directing developmental or elicitor/infection induced expression of said structural gene;

(b) transforming the plant cell with the vector of step (a); and (c) growing the plant cell of step (b) under conditions whereby structural gene expression is under the transcriptional control of the DNA segment comprising a portion of the isoflavone reductase promoter region;

wherein the portion of the isoflavone reductase promoter region is selected from the group consisting of about nucleotide 1 to about nucleotide 845 of the sequence depicted in SEQ ID NO: 1, about nucleotide 1 to about nucleotide 765 of the sequence depicted in SEQ ID NO: 1, about nucleotide 1 to about nucleotide 330 of the sequence depicted in SEQ ID NO: 1, about nucleotide 330 to about nucleotide 845 of the sequence depicted in SEQ ID NO: 1, and about nucleotide 330 to about nucleotide 765 of the sequence depicted in SEQ ID NO:1.

29. The method of claim 28 wherein the portion of the isoflavone reductase promoter region capable of directing developmental or elicitor/infection-induced expression comprises about nucleotide 1 to about nucleotide 845 of the sequence depicted in SEQ ID. NO: 1.

30. The method of claim 28 wherein the portion of the isoflavone reductase promoter region capable of directing developmental or elicitor/infection-induced expression comprises about nucleotide 1 to about nucleotide 765 of the sequence depicted in SEQ ID. NO: 1.

31. The method of claim 28 wherein the portion of the isoflavone reductase promoter region capable of directing developmental or elicitor/infection-induced expression comprises about nucleotide 1 to about nucleotide 330 of the sequence depicted in SEQ ID. NO: 1.

32. The method of claim 28 wherein the portion of the isoflavone reductase promoter region capable of directing developmental or elicitor/infection-induced expression comprises about nucleotide 330 to about nucleotide 845 of the sequence depicted in SEQ ID. NO: 1.

33. The method of claim 28 wherein the portion of the isoflavone reductase promoter region capable of directing developmental or elicitor/infection-induced expression comprises about nucleotide 330 to about nucleotide 765 of the sequence depicted in SEQ ID. NO: 1.

34. A method of expressing in a plant cell a structural gene, which is not naturally found in the plant cell, operably linked to a DNA segment comprising a portion of the isoflavone reductase promoter region capable of directing developmental or elicitor/infection-induced expression, said method comprising:

(a) inserting the structural gene which is not naturally found in the plant cell into a vector suitable for transforming plant cells so that the structural gene is operably linked to the DNA segment comprising a portion of the isoflavone reductase promoter region capable of directing developmental or elicitor/infection-induced expression of said structural gene;

(b) transforming the plant cell with the vector of step (a); and (c) growing the plant cell of step (b) under conditions whereby structural gene expression is under the transcriptional control of the DNA segment comprising a portion of the isoflavone reductase promoter region;

wherein the portion of the isoflavone reductase promoter region is selected from the group consisting of about nucleotide 1 to about nucleotide 845 of the sequence depicted in SEQ ID NO: 1, about nucleotide 1 to about nucleotide 765 of the sequence depicted in SEQ ID NO: 1, about nucleotide 1 to about nucleotide 330 of the sequence depicted in SEQ ID NO: 1, about nucleotide 330 to about nucleotide 845 of the sequence depicted in SEQ ID NO: 1, and about nucleotide 330 to about nucleotide 765 of the sequence depicted in SEQ ID NO: 1.

35. The method of claim 34 wherein the portion of the isoflavone reductase promoter region capable of directing developmental or elicitor/infection-induced expression comprises about nucleotide 1 to about nucleotide 845 of the sequence depicted in SEQ ID. NO: 1.

36. The method of claim 34 wherein the portion of the isoflavone reductase promoter region capable of directing developmental or elicitor/infection-induced expression comprises about nucleotide 1 to about nucleotide 765 of the sequence depicted in SEQ ID. NO: 1.

37. The method of claim 34 wherein the portion of the isoflavone reductase promoter region capable of directing developmental or elicitor/infection-induced expression comprises about nucleotide 1 to about nucleotide 330 of the sequence depicted in SEQ ID. NO: 1.

38. The method of claim 34 wherein the portion of the isoflavone reductase promoter region capable of directing developmental or elicitor/infection-induced expression comprises about nucleotide 330 to about nucleotide 845 of the sequence depicted in SEQ ID. NO: 1.

39. The method of claim 34 wherein the portion of the isoflavone reductase promoter region capable of directing developmental or elicitor/infection-induced expression comprises about nucleotide 330 to about nucleotide 765 of the sequence depicted in SEQ ID. NO: 1.

* * * * *

UNITED STATES PATENT AND TRADEMARK OFFICE
CERTIFICATE OF CORRECTION

PATENT NO. : 5,750,399
DATED : May 12, 1998
INVENTOR(S) : Richard A. Dixon, et al.

It is certified that error appears in the above-indentified patent and that said Letters Patent is hereby corrected as shown below:

Col 1, line 65, change "phenylalanine ammonia-lyase-α-glucuronidase" to --phenylalanine ammonia-lyase-β-glucuronidase--.

Col 6, line 8, change "MgCl2" to --$MgCl_2$--.

Col 7, line 28, after "DH5α", delete --u--.

Col 7, line 63, before "for", change "All" to --A11--.

Col 20, line 3, claim 13, after "7" insert --,--.

Signed and Sealed this

Fifteenth Day of September, 1998

*Attest:*

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
 ( A ) LENGTH: 2730 base pairs
 ( B ) TYPE: nucleic acid
 ( C ) STRANDEDNESS: both
 ( D ) TOPOLOGY: linear ( i i ) MOLECULE TYPE: DNA (genomic)

( x i ) SEQUENCE DESCRIPTION: SEQ ID NO:1:

```
ACTAGTTTTG TAAGAATTTT TTGAAACTTG TGTAATCCAA TATTAAAAAA TGTAAAAAAA        60

AATGTTATCT TTTATACAAA ACTTACCTTT TATGTTTCTT TAACTAATGC CTTAAAGATA       120

CCGATTAACA TCCAATAATT AAATACCACC TAACATCAAC AATTACAAAG AAATAACAAC       180

CTATTGAAAC TCATTGCAAA CGCTCTAACT TGCAAACTTT CTTTGAGAA AGTATTTTTT        240

ATTTAACTTT CTAGGTGTTG AAGAACAATT TATGTTGAGT GAATATTAAA CACATTTTTT       300

TATAATAGTT GAATCTATCA AATGAAGACG AATTCAACAT GCAGGTTGGG TTGTGTCATT       360
```

```
GTTAAAAAGT TGTGAAGTAA AGGTTTCAAG TTGAATATTT AAAAAATCCT TAAAAAAGTT    420
ATATGTATAT ATCATGTTAA TAATAATAAT TAGTATAAAT CGGTGTATTC TTTTGTTCTC    480
TTTGCTAAGA TATATTCTTG CTTCCGGCCA AGTTTTCAGC AGAATTGTTT GATAAGTAGA    540
GTTTTTTTAT ATATATTTTA ACTGACTACT AATATGTTTT ATACGGAGTT AATTAAGTAG    600
ACTTAAGAGA AGGCGTCAAT TTTGACCAAC AGGGCTGCTT CTATTTCAAC AACAATGAAT    660
ATTAAATTTG GTCACTAAAA CACACAGAGA GTAGTAGATG GATTGAAGTT GGTGGCAATC    720
CAAGTTTGTC CTATAAATAT CAAACAAGT ATAGCTATTC ATCACACACT CACTACTACT    780
TTGGTAACGT ATTCAAAACA AGAAAAAACA GACAAAAACA TAAACACACT TGTTTTTTTA    840
CTAGTTATTT TTTTCCAATG GCAACTGAAA ACAAAATCCT GATCCTAGGA CCAACAGGAG    900
CTATTGGAAG ACACATAGTT TGGGCAAGTA TTAAAGCAGG AAATCCAACA TATGCTTTGG    960
TTAGAAAAAC ACCTGGCAAT GTTAACAAGC CAAAGCTTAT TACAGCTGCT AATCCTGAAA   1020
CCAAGGAAGA GCTTATTGAT AATTACCAAT CTTTAGGAGT TATTCTACTT GAAGTAAGTG   1080
ATTTCAATAT GTGAAATAAT TTATATTCT ATATATTTAT TAAATTGACC TAATCAATAT   1140
GTCTTTGACT CTGCAGGGTG ATATAAATGA TCATGAAACT CTTGTTAAGG CAATCAAGCA   1200
AGTTGACATT GTGATCTGTG CTGCTGGTAG ACTACTAATT GAAGATCAGG TCAAGATTAT   1260
TAAAGCAATT AAAGAAGCTG GAAACGTTAA GGTGAACAAA TTTGTCACTA CACCAGTAAA   1320
TAAGTCCAAA TAAGTCAATT CATATAGAGT CTTAGTTAGT AATAACTCTT TGATGGTTAG   1380
ATTTGTACTC GTTATATTGA ATAGTGGTAC TAAATTTCTT GTGTCGACAG AAATTTTTCC   1440
CATCTGAATT TGGGCTAGAC GTGGACCGTC ATGAGGCCGT TGAGCCAGTT AGACAAGTTT   1500
TTGAAGAAAA AGCAAGTATC CGAAGAGTAA TTGAAGCCGA AGGAGTTCCT TACACTTACC   1560
TTTGTTGCCA CGCCTTTACC GGTTACTTCT TACGTAACTT GGCTCAACTC GACACAACTG   1620
ATCCTCCTCG GGACAAAGTT GTCATTCTTG GAGATGGAAA TGTGAAAGGT AACAGACTTA   1680
GTCACAGAAC AATTCAACAA ACTAGTATTG AACAAAGAC ACACAATTCA GTTGTTTCAA   1740
TAATTATACC TTACTCATTT CAGGAGCATA TGTAACTGAG GCTGATGTGG AACTTTTAC   1800
CATTAGAGCA GCAAATGATC CCAACACATT GAACAAAGCT GTCCATATTA GACTCCCCGA   1860
AAATTATTTG ACCCAAAATG AGGTCATTGC CCTTTGGGAG AAAAAGATTG GAAGACTCT   1920
TGAGAAAACT TATGTTTCAG AGGAACAAGT TCTCAAGGAT ATTCAAGGTC AGTAAAATAA   1980
ACGCTTTATA AATATTGTTA AGAATTTTA CACCGGTAAT CAATCATAGT TGATAAATCG   2040
TTAAAAATAT TTGATTTTAA TTATATCTAT TTAATGACC GCACAAATAT CTGACGGTGT   2100
ATCAAAATTA ATCTCTTAGT GTTAAATTAT GAGTGACATG TATGTCATTT TACAGCAATT   2160
TTGTAAAATT AATCATGAAA TATGTTACTT GCTATGCAGA ATCTTCATTC CCTCATAACT   2220
ATTTGTTGGC ATTGTACCAT TCACAACAAA TAAAAGGAGA TGCAGTGTAT GAGATTGATC   2280
CAGCCAAAGA TATTGAAGCT TCTGAAGCCT ATCCAGATGT GACATACACC ACTGCTGATG   2340
AATATTTGAA TCAATTTGTC TAACGAATGC TAAGGAAATG TTCAATAAGA CAATGAATTT   2400
AAAAAAAAAA AAGTTTCACA TCTGTGTATG TTTCTTGTGT TTGTTTAGTT TTGTTCTCAG   2460
TAATCCCTCC CAATTGATGT AATAATTTAC AAAAATAATA AATATTATAT TCTGTTCCAC   2520
TGTTTGCACA TCTTTGTCTC TTTGTTCAAT ATTTTACATT GTGGCTTCTC ATTTTATGCG   2580
TCACTGTGAA GGGCCGACTC CAAAAATAAT TAAACGCACG CCCAAAATGG ACTGAAAAAT   2640
TCACTAATTA GACAAGTAGA AATATAATAA GAACTGAAAT AATGACGAAA AAAAAATAAG   2700
AACTAAAAAA AATAGAAATA TTAGGAATTC                                    2730
```